(12) United States Patent
Wu

(10) Patent No.: US 10,883,904 B2
(45) Date of Patent: Jan. 5, 2021

(54) AUTOMATIC WETTING APPARATUS

(71) Applicant: Fineetex (DongGuan) Co., Ltd., Dongguan (CN)

(72) Inventor: Xumin Wu, Dongguan (CN)

(73) Assignee: FINEETEX (DONGGUAN) CO., LTD., Dongguan (CN)

( * ) Notice: Subject to any disclaimer, the term of this patent is extended or adjusted under 35 U.S.C. 154(b) by 39 days.

(21) Appl. No.: 16/423,095

(22) Filed: May 27, 2019

(65) Prior Publication Data

US 2019/0277732 A1 Sep. 12, 2019

(30) Foreign Application Priority Data

Feb. 28, 2019 (CN) .......................... 2019 1 0154614

(51) Int. Cl.
*G01N 1/31* (2006.01)
*B05B 14/00* (2018.01)
*B05B 9/04* (2006.01)
*G01N 33/36* (2006.01)

(52) U.S. Cl.
CPC ........... *G01N 1/312* (2013.01); *B05B 9/0413* (2013.01); *B05B 14/00* (2018.02); *G01N 33/367* (2013.01); *G01N 2001/317* (2013.01)

(58) Field of Classification Search
CPC ... B05B 13/0242; B05B 14/00; B05B 9/0413; G01N 1/312; G01N 2001/317; G01N 33/367
See application file for complete search history.

(56) References Cited

U.S. PATENT DOCUMENTS

| | | | | |
|---|---|---|---|---|
| 6,629,539 B1 * | 10/2003 | Yanagita | ........... | H01L 21/67196 134/134 |
| 7,442,296 B2 * | 10/2008 | Chong | .................... | E03C 1/264 210/163 |
| 2014/0041689 A1 * | 2/2014 | Namba | ............. | H01L 21/67051 134/22.1 |

* cited by examiner

*Primary Examiner* — Jennifer Wecker
*Assistant Examiner* — Pallavi Chitta
(74) *Attorney, Agent, or Firm* — Shimokaji IP

(57) ABSTRACT

An automatic wetting apparatus includes a frame, and a wetting device, an air blowing device, a driving device and a station turntable. The frame is provided with a loading station, an wetting station, a unloading station and an air blowing station, the driving device includes an output end connected with the station turntable, the wetting device is cooperated with the wetting station, the air blowing device is cooperated with the air blowing station, the station turntable is provided with a support unit, the support unit is provided with a through hole, and the support unit is selectively rotatable to align with the loading station, the wetting station, the unloading station or the air blowing station, under an action of the driving device. The processes for loading, wetting and unloading are coherent, and the wetting accuracy and the wetting efficiency are high.

8 Claims, 5 Drawing Sheets

AUTOMATIC WETTING APPARATUS

RELATED APPLICATIONS

This application claims the benefits of Chinese Patent Application No. 201910154614.8, filed Feb. 28, 2019, the entire contents of which are hereby incorporated by reference in this application.

FIELD OF THE INVENTION

The present invention relates to the field of detection, and more particularly to an automatic wetting apparatus for detecting color fastness of fabric sheets.

BACKGROUND OF THE INVENTION

With the rapid development of society, various mechanical manufacturing processes are becoming more and more mature. Some semi-automatic or automated machines are widely used in various industries due to their high efficiency and high operational precision.

It is well known that in the field of detection, it's necessary to detect the color fastness of the fabric. Color fastness is also called dye fastness which refers to the resistance of the color of textiles to various effects during processing and use. The fastness grade is determined based on the discoloration of the sample and the staining of the undyed adjacent fabric. The textile color fastness test is a routine test item in the textile intrinsic quality test. The performance of the color fastness directly relates to the health and safety of the human body. The product with poor color fastness will fall off and fade when the clothes are hit by the rain or sweat, and the molecules of the dye and the heavy metal ions, etc. may be absorbed by the body and endanger the health of the human skin. On the other hand, other clothes may be stained possibly, thus the color fastness is an important factor of the fabrics.

The existing color fastness detection includes dry rub detection and wet rub detection. For wet rub detection, the existing operation steps mainly include: first, performing precise quantitative wet spraying operation on the test fabric sheet; and then letting the test fabric sheet stand for a while, and then putting it on the weighing instrument after it is completely absorbed to ensure that the test fabric sheet absorbs the quantitative water and reaches the detection condition; then, placing the water-absorbed test fabric sheet on the wiping device and wiping test the fabric sheet and a reference fabric sheet back and forth; finally, comparing the wiped test fabric sheet and the reference fabric sheet with the color chart, so as to determine the degree of color fastness of the test fabric sheet.

However, since it is necessary to spray a certain amount of water on the test fabric sheet during the wet spraying operation of the test fabric sheet, in the process, it is necessary to ensure that the water absorption amount (namely the humidification amount) of the test fabric sheet reaches the test standard before the subsequent detection. For example, it is required to meet the humidification standard of the American Association of Dyers and Chemists (AATCC) or the International Standards Organization (ISO) humidification standard, so this process requires precise control of the amount of water spray, therefore the existing wetting process to the test fabric sheets is performed manually. However, such a manual wetting and wetting is very inefficient since it's necessary to clean after each wetting process for each test fabric sheet. Further, it may cause excessive wetting in the manual wetting process.

Therefore, there is a need to provide an automatic wetting apparatus which has high immersion accuracy and high immersion efficiency.

SUMMARY OF THE INVENTION

One objective of the present invention is to provide an automatic wetting apparatus which has high wetting accuracy and high wetting efficiency.

To achieve the mentioned above objectives, the present invention provides an automatic wetting apparatus comprising a frame, and a wetting device, an air blowing device, a driving device and a station turntable configured on the frame respectively. The frame is provided with a loading station, an wetting station, a unloading station and an air blowing station which are arranged apart along a circumferential direction of the station turntable, the driving device comprises an output end connected with the station turntable, the wetting device is cooperated with the wetting station, the air blowing device is cooperated with the air blowing station, the station turntable is provided with a support unit for supporting fabric sheets, the support unit is provided with a through hole running through the station turntable along a height direction of the station turntable, and the support unit is selectively rotatable to align with the loading station, the wetting station, the unloading station or the air blowing station, under an action of the driving device.

Preferably, the frame comprises a base and a mounting frame mounted on the base, the base is provided with a receiving space in which the driving device is installed, the station turntable is mounted on the base, the output end of the driving device is protruded from the base and connected with the station turntable, the wetting device and the air blowing device are mounted on the mounting frame and located above the station turntable.

Preferably, the apparatus further comprises a support frame that is latticed, and the support frame is detachably placed on the support unit to cover the through hole.

Preferably, the support unit has an upper surface which is provided with a tilted part surrounding the through hole, and the tilted part is tilted towards the through hole.

Preferably, the base comprises a base support and a guide plate, the guide plate is tightly covered on the base support to define the receiving space for receiving the driving device, the station turntable is located above the guide plate, and the output end of the driving device passes through the guide plate and is connected with the station turntable.

Preferably, the base further comprises an outer ring structure and an inner ring structure surrounded by the outer ring structure, an annular fluid directing space is defined between the outer ring structure and the inner ring structure, the guide plate is tightly pressed against a top of the inner ring structure, and a middle part of the guide plate is bulged.

Preferably, an annular connecting portion is configured at the fluid directing space, one end of the connecting portion is connected with a bottom of the inner ring structure, and another end of the connecting portion is connected with the outer ring structure.

Preferably, the base further comprises a liquid collecting tank located in the receiving space, a guiding hole is configured on the connecting portion, and the liquid collecting tank is located right below the guiding hole.

Preferably, a notch is formed on a side wall of the base support.

Preferably, the wetting device comprises a bottle, a nozzle and a piston pump for pumping water in the bottle to the nozzle.

In comparison with the prior art, since the frame of the automatic wetting apparatus is arranged with the loading station, the wetting station, the unloading station and the air blowing station, and the support unit is selectively rotatable to align with the loading station, the wetting station, the unloading station or the air blowing station under an action of the driving device; therefore the operation processes of loading, wetting and unloading of the fabric sheets are coherent, and the blowing process to the support unit is ensured after each loading, so as to avoid residual liquid from affecting the fabric sheet to be loaded next time. Specifically, the wetting device is cooperated with the wetting station, the air blowing device is cooperated with the air blowing station, and the support unit for carrying the fabric sheets is provided on the station turntable, and the support unit is provided with a through hole extending through the station turntable along the height direction of the station turntable, so as to guide the residual liquid remaining on the station turntable through the through hole by means of the air blowing device.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
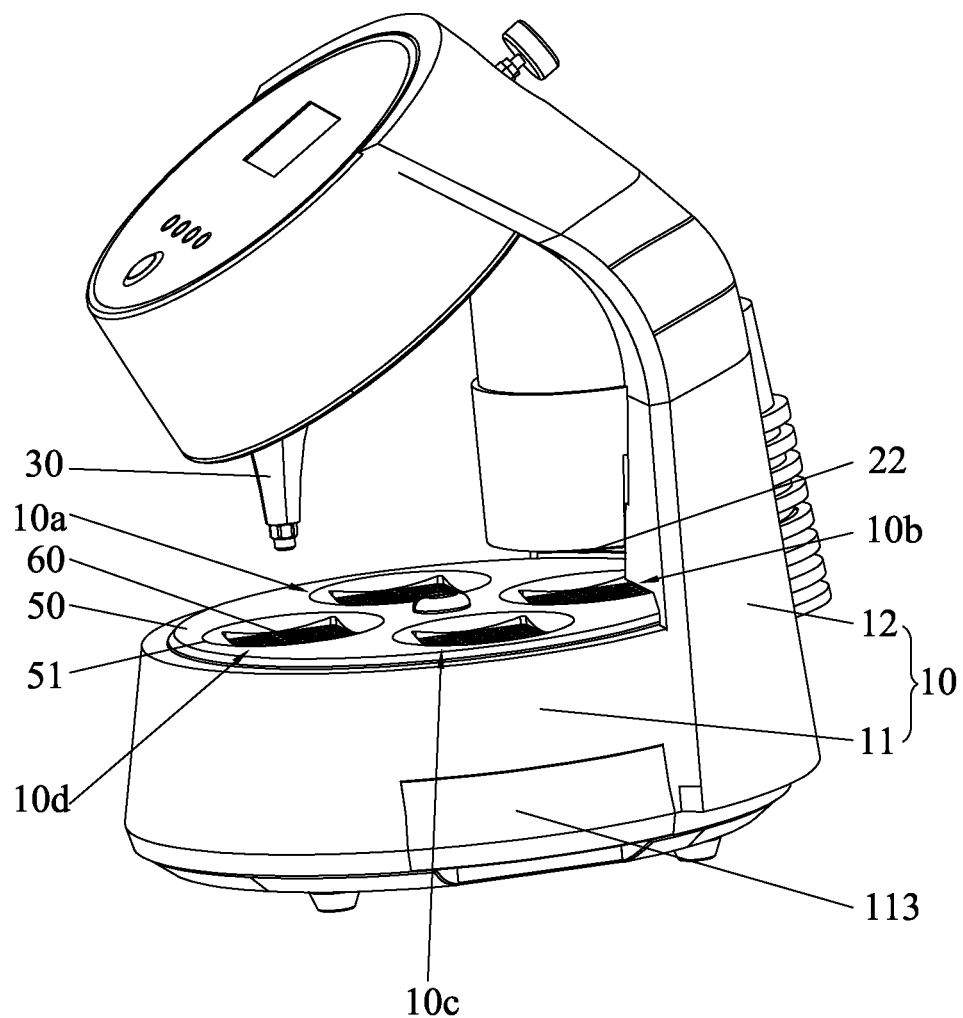
FIG. 1 is a perspective view of an automatic wetting apparatus according to an embodiment of the present invention.

The present invention will be described in detail below with reference to the accompanying drawings and preferred embodiments.

As illustrated in FIGS. 1-6, an automatic wetting apparatus 100 of the present invention includes a frame 10, and an wetting device 20, an air blowing device 30, a driving device 40 and a station turntable 50 configured on the frame 10 respectively. The frame 10 is provided with a loading station 10a, an wetting station 10b, an unloading station 10c and a air blowing station 10d which are arranged apart along a circumferential direction of the station turntable 50, the driving device 40 includes an output end connected with the station turntable 50, the wetting device is corresponding with the wetting station, the air blowing device is corresponding with the air blowing station, the station turntable is provided with a support unit for supporting fabric sheet, the support unit is provided with a through hole running through the station turntable along a height direction of the station turntable, and the support unit 51 is selectively rotatable to align with the loading station 10a, an wetting station 10b, a unloading station 10c or a air blowing station 10d, under an action of the driving device 40.

Referring to FIGS. 1-6 again, the frame 10 includes a base 11 and a mounting frame 12 mounted on the base 11, the base 11 is provided with a receiving space 11a in which the driving device 40 is installed, the station turntable 50 is mounted on the base 11, the output end of the driving device 40 is protruded from the base 11 and connected with the station turntable 50, the wetting device 20 and the air blowing devices 30 are mounted on the mounting frame 12 and located above the station turntable 50. When the air blowing device 30 blows the support unit 51, the liquid remained on the working turntable 50 is guided through the through hole 51a under the action of the air press and the gravity, thus the cleaning ability of the station turntable 50 is improved. It should be noted that, the wetting device 20 can be installed below the station turntable 50 according to the actual demands, and the air blowing device 30 also can be installed below the station turntable 50, which is not limited here. Specifically, the wetting device 20 is located right above the support unit 51 of the wetting station 10b, and the air blowing device 20 is located right above the support unit 51 of the air blowing station 10d, which is not limited here.

Referring to FIGS. 1-4, the automatic wetting apparatus further includes a support frame 60 that is latticed, and the support frame 60 is detachably placed on the support unit 51 to cover the through hole 51a. In the actual use, the fabric sheet is placed on the support frame 60, the liquid remained on the station turntable 50 will flow through the support frame 60 as it is latticed and hollow, and through the through hole 51a in turn, so as to be guided away. Specifically, the side wall of the through hole 51a is extended towards the center direction to form a support portion 52 for supporting the support frame 60. That is, the support frame 60 is disposed on the support portion 52. When there is a need to remove the support frame 60 from the station turntable 50 to clean, it is only necessary to take the support frame 60 directly upward along the through hole 51a. by this token, the installation, the disassembly, the maintain and the replacement of the support frame 60 are convenient.

Figure 3:
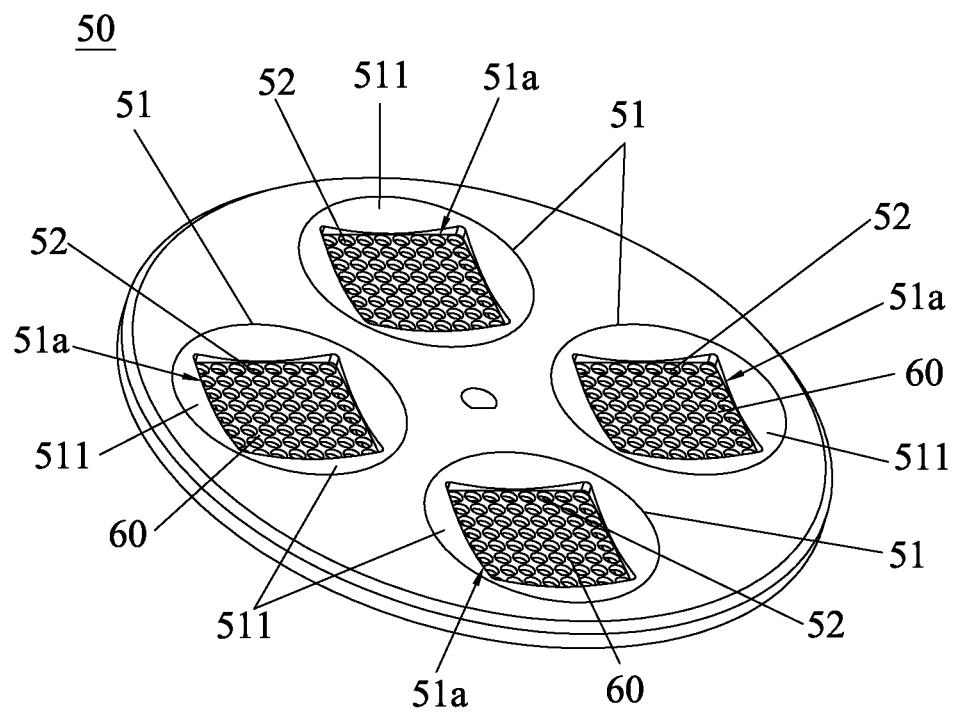
FIG. 3 is a perspective view of a station turntable of the automatic wetting apparatus according to an embodiment of the present invention.
Figure 4:
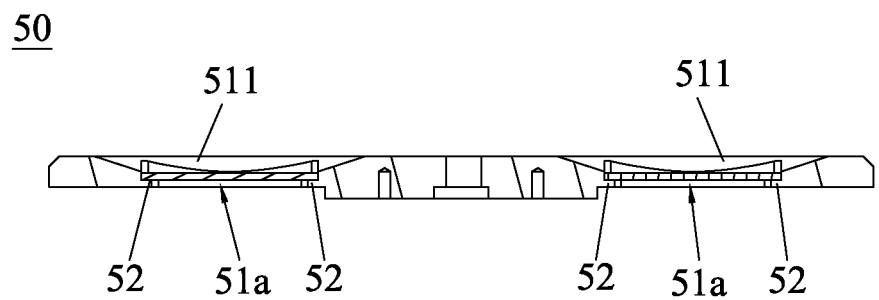
FIG. 4 is a sectional view of the station turntable of the automatic wetting apparatus according to an embodiment of the present invention.

Referring to FIGS. 3 and 4, the upper surface of the support unit 51 is configured with a tilted part 511 surrounding the through hole 51a, and the tilted part 511 is tilted towards the through hole 51a. When the liquid is spurted from the wetting device 20 and sprinkled on the tilted part 511, the liquid will drop on the fabric sheet placed on the support unit 51 due to the gravity action, in such a way, the liquid spurted from the wetting device 20 can be almost collected on the fabric sheet, meanwhile the blowing action of the air blowing device 30 is facilitated.

Figure 5:
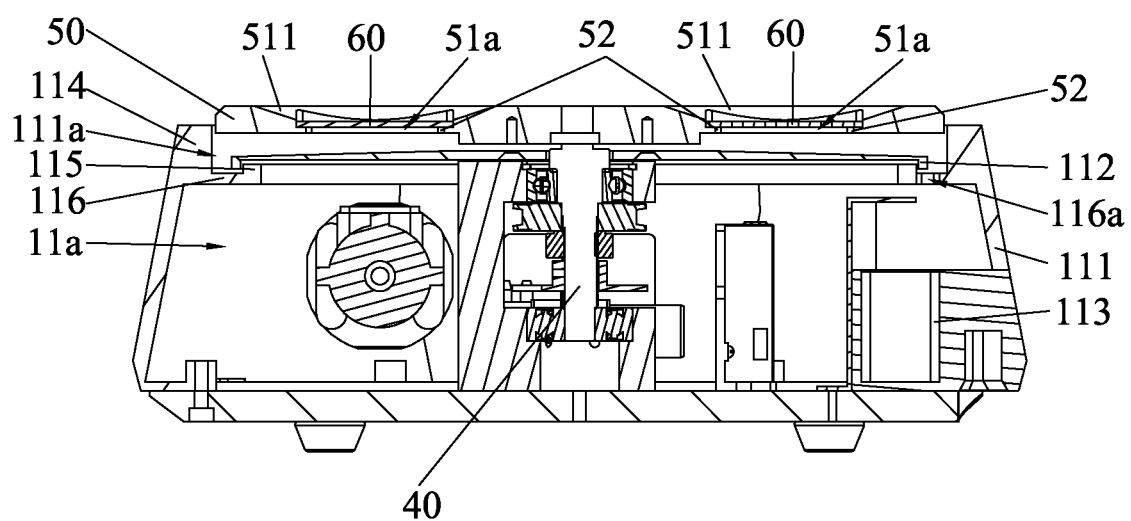
FIG. 5 is a sectional view of the base and the station turntable of the automatic wetting apparatus according to an embodiment of the present invention.
Figure 6:
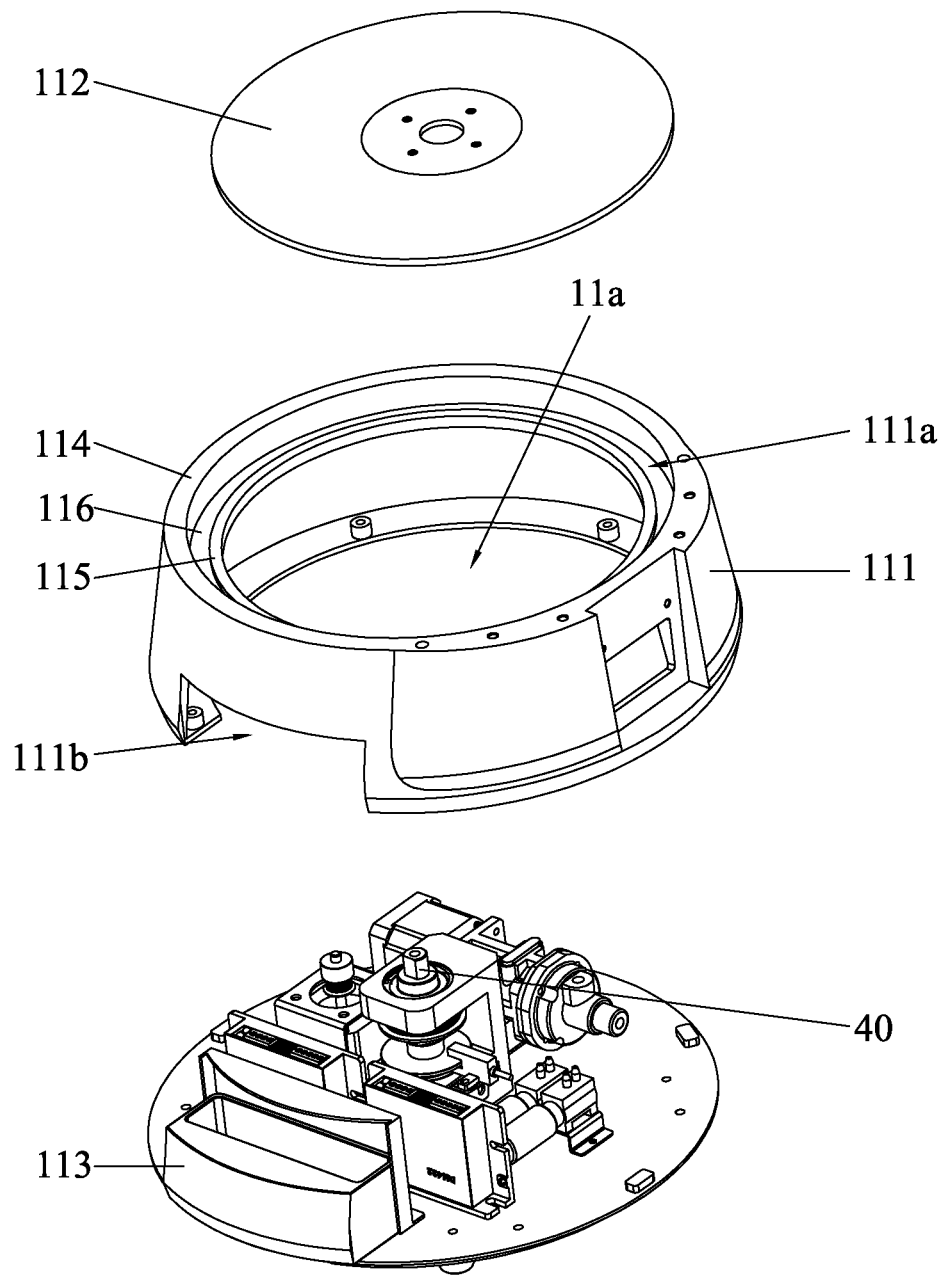
FIG. 6 is an exploded view of the base of the automatic wetting apparatus according to an embodiment of the present invention.

Referring to FIGS. 5 and 6, the base 11 includes a base support 11, a guide plate 112 and a liquid collecting tank 113. The guide plate 112 is tightly covered on the base support 111 to define the receiving space 11a for receiving the driving device 40, the station turntable 50 is located above the guide plate 112, and the output end of the driving device 40 passes through the guide plate 112 and is connected with the station turntable 50. Since the guide plate 112 is tightly covered on the base support 111, thus the liquid is prevented from dropping to the driving device 40 to damage the driving device 40. The base support 111 includes an outer ring structure 114 and an inner ring structure 115 surrounded by the outer ring structure 114, an annular fluid directing space 111a is defined between the outer ring structure 114 and the inner ring structure 115, the guide plate 112 is tightly pressed against a top of the inner ring structure 115, and a middle part of the guide plate 112 is bulged. As a result, the liquid dropping on the guide plate 112 will be guided to the fluid directing space 111a, due to the guiding action of the guide plate 112. Preferably, an annular connecting portion 116 is configured at the fluid directing space 111a, one end of the connecting portion 116 is connected with a bottom of the inner ring structure 115, and another end of the connecting portion 116 is connected with the outer ring structure 114. A guiding hole 116a is formed on the connecting portion 116. The liquid collecting tank 113 is located in the receiving space 111a and right below the guiding hole 116a, thus the liquid slid in the fluid directing space 111a will flow through the guiding hole 116a, finally will be collected by the liquid collecting tank 113. That is, the outer ring structure 114, the connecting portion 116 and the inner ring structure form an annular diversion trench, as a result, the liquid dropping o the guide plate 112 will flow along the guide plate 112 to the connecting portion 116. More specifically, the guiding hole 116a is formed on the connecting portion 116, and the liquid collecting tank 113 is located right below the guide hole 116a, thus the liquid on the connecting portion 116 will finally flow through the guide hole 116a to drop into the liquid collecting tank 113. Specifically, the side wall of the base support 111 is formed with a notch 111b for allowing the liquid collecting tank 113 to slide. When the liquid collecting tank 113 is filled with liquid, user may pull out the tank 113 to clean.

Figure 2:
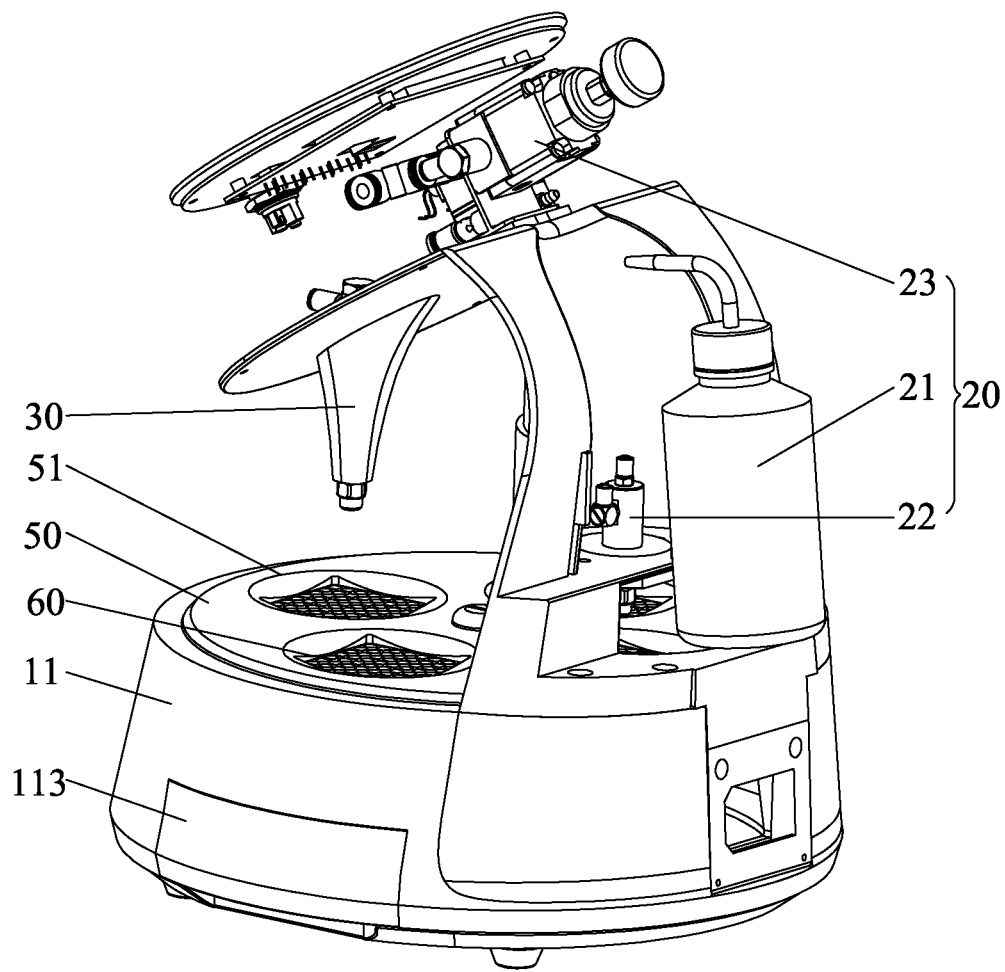
FIG. 2 is a perspective view of the automatic wetting apparatus with a mounting frame is removed according to an embodiment of the present invention.

Referring to FIG. 2, the wetting device 20 includes a bottle 21 for filling with water, a nozzle 22 and a piston pump 23 for pumping water in the bottle 21 to the nozzle 22. By means of the piston pump 23, the quantity of the water in the bottle 21 can be controlled accurately, so as to further ensure the precise quantitative wet spraying to the fabric sheet. For example, the nozzle 22 can spray water downwards in a range of about 120 degrees, so as to achieve uniform wetting of various parts of the fabric sheet.

In comparison with the prior art, since the frame 10 of the automatic wetting apparatus according to the present invention is provided with the loading station 10a, the wetting station 10b, the unloading station 10c and the air blowing station 10d, and the support unit 51 on the station turntable 50 is selectively rotatable to align with the loading station 10a, the wetting station 10b, the unloading station 10c or the air blowing station 10d under an action of the driving device 40; therefore the operation processes of loading, wetting and unloading of the fabric sheets are coherent, and the blowing process to the support unit 51 is ensured after each loading process, so as to avoid residual liquid from affecting the fabric sheet to be loaded next time. Specifically, the wetting device 20 is cooperated with the wetting station 10b, the air blowing device 30 is cooperated with the air blowing station 10d, and the support unit 51 for carrying the fabric sheets is provided on the station turntable 50, and the support unit 51 is provided with a through hole 51a extending through the station turntable 50 along the height direction of the station turntable 50, so as to guide the residual liquid remaining on the station turntable 50 through the through hole 51a by means of the air blowing device 30.

The foregoing description of the present invention has been presented for purposes of illustration and description. It is not intended to be exhaustive or to limit the invention to the precise form disclosed, and obviously many modifications and variations are possible in light of the above teaching. Such modifications and variations that may be apparent to those skilled in the art are intended to be included within the scope of this invention as defined by the accompanying claims.

What is claimed is:

1. An automatic wetting apparatus, comprising a frame, and a wetting device, an air blowing device, a driving device and a station turntable configured on the frame respectively, wherein the frame is provided with a loading station, a wetting station, an unloading station and an air blowing station which are arranged apart along a circumferential direction of the station turntable, the driving device comprises an output end connected with the station turntable, the wetting device is cooperated with the wetting station, the air blowing device is cooperated with the air blowing station, the station turntable is provided with a support unit for supporting fabric sheets, the support unit is provided with a through hole running through the station turntable along a height direction of the station turntable, and the support unit is selectively rotatable to align with the loading station, the wetting station, the unloading station or the air blowing station, under an action of the driving device;
   wherein the frame comprises a base and a mounting frame mounted on the base, the base is provided with a receiving space in which the driving device is installed, the station turntable is mounted on the base, the output end of the driving device is protruded from the base and connected with the station turntable, the wetting device and the air blowing device are mounted on the mounting frame and located above the station turntable;
   wherein the base comprises a base support and a guide plate, the guide plate is tightly covered on the base support to define the receiving space for receiving the driving device, the station turntable is located above the guide plate, and the output end of the driving device passes through the guide plate and is connected with the station turntable.

2. The automatic wetting apparatus according to claim 1, further comprising a support frame that is latticed, and the support frame is detachably placed on the support unit to cover the through hole.

3. The automatic wetting apparatus according to claim 1, wherein the support unit has an upper surface which is provided with a tilted part surrounding the through hole, and the tilted part is tilted towards the through hole.

4. The automatic wetting apparatus according to claim 1, wherein the base further comprises an outer ring structure and an inner ring structure surrounded by the outer ring structure, an annular fluid directing space is defined between the outer ring structure and the inner ring structure, the guide plate is tightly pressed against a top of the inner ring structure, and a middle part of the guide plate is bulged.

5. The automatic wetting apparatus according to claim 4, wherein an annular connecting portion is configured at the fluid directing space, one end of the connecting portion is connected with a bottom of the inner ring structure, and another end of the connecting portion is connected with the outer ring structure.

6. The automatic wetting apparatus according to claim 5, wherein the base further comprises a liquid collecting tank located in the receiving space, a guiding hole is configured on the connecting portion, and the liquid collecting tank is located right below the guiding hole.

7. The automatic wetting apparatus according to claim 6, wherein a notch is formed on a side wall of the base support.

8. The automatic wetting apparatus according to claim 1, wherein the wetting device comprises a bottle, a nozzle and a piston pump for pumping water in the bottle to the nozzle.

\* \* \* \* \*